United States Patent
Maaskamp et al.

[11] Patent Number: 6,013,046
[45] Date of Patent: Jan. 11, 2000

[54] SLEEVE SHIELDED NEEDLES FOR PHACO-EMULSIFICATION DEVICES

[75] Inventors: Armand Maaskamp; Alex Urich, both of Mission Viejo, Calif.

[73] Assignee: Surgin Surgical Instrumentation, Inc., Tustin, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/732,030

[22] Filed: Oct. 16, 1996

[51] Int. Cl.7 .................................................. A61M 5/158
[52] U.S. Cl. .............................. 604/22; 604/282; 606/169
[58] Field of Search ........................... 604/22, 282, 268; 606/169, 170, 171

[56] References Cited

U.S. PATENT DOCUMENTS

| | | |
|---|---|---|
| 3,938,529 | 2/1976 | Gibbons .............................. 604/282 X |
| 4,052,989 | 10/1977 | Kline .................................. 604/282 X |
| 4,515,583 | 5/1985 | Sorich . |
| 4,634,420 | 1/1987 | Spinosa et al. . |
| 4,787,889 | 11/1988 | Steppe et al. . |
| 4,808,154 | 2/1989 | Freeman . |
| 4,869,715 | 9/1989 | Sherburne . |
| 4,955,862 | 9/1990 | Sepetka .............................. 604/282 X |
| 5,180,376 | 1/1993 | Fischell ................................. 604/282 |
| 5,282,786 | 2/1994 | Ureche ................................... 604/22 |
| 5,286,256 | 2/1994 | Mackool . |
| 5,308,342 | 5/1994 | Sepetka et al. ........................ 604/282 |

*Primary Examiner*—Michael H. Thaler
*Attorney, Agent, or Firm*—Konrad, Raynes & Victor

[57] ABSTRACT

A sleeve-shielded needle, to be inserted through an incision for maintenance of aspiration and irrigation flows includes a soft sleeve portion about a small diameter needle tip, at a spacing sufficient to provide a flow gap for irrigation fluid while aspiration fluid flows oppositely through the center of the needle tip. A radially rigid tubular element within a proximal portion of the sleeve maintains a constant flow gap, allowing the edges of a small incision into which the needle is inserted to compress the soft sleeve without reducing the gap. At the distal end, however, the sleeve can compress in response to tissue resistance during insertion, minimizing the risks of tearing tissue or enlarging the incision.

10 Claims, 3 Drawing Sheets

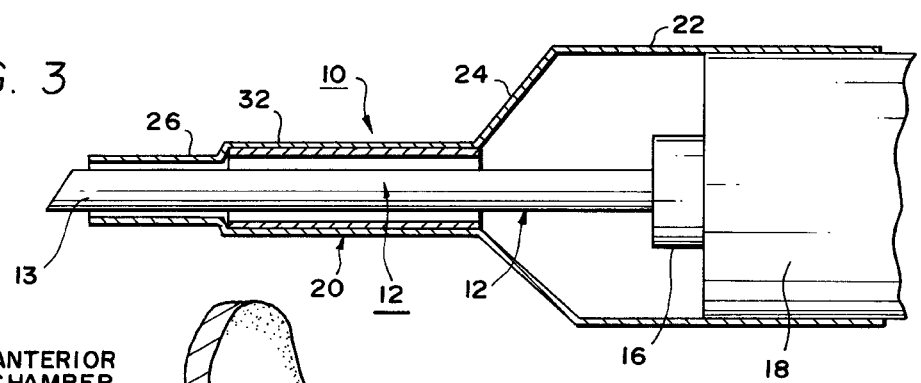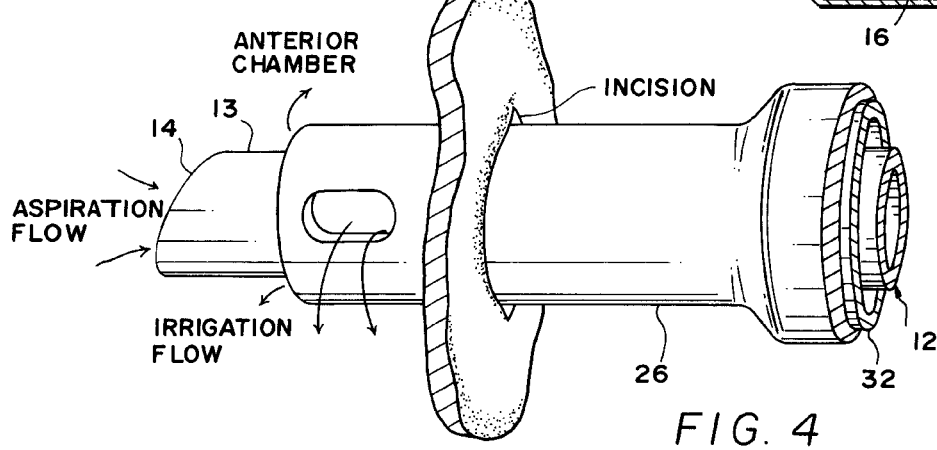

SLEEVE SHIELDED NEEDLES FOR PHACO-EMULSIFICATION DEVICES

FIELD OF THE INVENTION

The present invention relates to surgical apparatus and more particularly to phaco-emulsification and other surgical needles that are disposed within outer sleeves, and the problem of efficiently irrigating the eye chamber via a minute opening without excessive leakage or tissue damage.

BACKGROUND OF THE INVENTION

Surgical procedures that are carried out within the anterior chamber of the eye require at least one penetrating incision passing through the peripheral tissues of the eye such as the cornea and the sclera. One such procedure is the removal of a cataract by ultrasonic fragmentation and aspiration (phaco-emulsification) through a small-diameter ultrasonically-vibrated needle having a central aspiration conduit. During surgery the top of the needle is inserted through an incision just large enough to accommodate the diameter of the tip. Typically, incisions of about 3 mm or less are used. As aqueous humor is removed by aspiration through the ultrasonic needle tip and fluid leaks out of the incision, the fluid must be replaced or the anterior chamber of the eye will collapse. Other small needles may be used in ophthalmic and other surgery that do not employ ultrasonic vibration, but still aspirate the fluid in a chamber.

In order to prevent these problems, irrigating fluid is constantly supplied to the interior of the eye, either through a secondary incision in the eye or by irrigation and aspiration through an outer irrigation channel. The irrigation channel is usually formed about the exterior of the needle by adding an outer sleeve which fits clearly over the needle. Such sleeves are presently of a soft elastomeric material so that they can conform to the incision and compress at the distal end. Either radial or axial compression of the sleeve can cause blockage of irrigation flow, however, and it is essential to maintain flow under all conditions of operation. Moreover, with ultrasonically energized needles, if cooling fluid flow diminishes, frictional heat increases because it cannot be dissipated. The heat build-up is sudden and pronounced, and can cause scleral or corneal burns very quickly.

A number of designs have been developed to prevent such reduction in fluid flow. One such design uses a rigid sleeve material to prevent collapse of the sleeve during surgery (U.S. Pat. No. 4,983,160). However, this design does not promote conformity and sealing between the peripheral tissue at the incision in the eye and the outside of the sleeve. Consequently, there can be excessive leakage of fluid from the eye during surgery. Also this design loses the desired flexibility of the tip on the sleeve. In another sleeve version (U.S. Pat. No. 5,282,786) a rigid portion is added to the exterior of the sleeve. While this design prevents collapse of the sleeve it too results in a poor seal and excessive leakage from the incision. Also such a product is expensive to manufacture, requiring specially molded parts to include the rigid portion into the sleeve. In another configuration (U.S. Pat. No. 4,808,154), ridges are included on the interior of the sleeve. However, in use, the ridges, in a soft polymeric material, are insufficient to prevent collapse of the sleeve and reduction in the flow rate of fluid. As seen in U.S. Pat. No. 5,286,256, two sleeves have also been used, one of a polymeric material to seal against the incision and the second, a rigid sleeve to prevent collapse of the fluid conduit. However, such a unit is bulky, requiring a larger incision which can result in longer healing time and distortions in the refractive qualities of the eye. It also does not facilitate maintenance of distal end flexibility or permit full transverse flow through side ports near the distal end. These are often used to isolate irrigation from aspiration flows so that irrigation fluid is not immediately drawn into the aspiration tip.

It is desirable to provide a sleeve arrangement for an aspiration needle which seals adequately against the periphery of the incision in the eye to reduce fluid loss but which does not collapse under the pressure of the incision or tissue. It is also desirable that this combination be inexpensive to manufacture, compatible with existing flexible sleeve elements, and suitable for use with different-sized needles.

SUMMARY OF THE INVENTION

The present invention provides an aspiration needle and encompassing sleeve combination for maintaining an irrigation flow about the aspiration tip for a surgical apparatus. The device comprises a sleeve of soft flexible material including an enlarged proximal bore portion for mounting on the needle and an internal small bore distal portion along the same axis. An interior tube is frictionally engaged within a proximal length of the distal portion. The interior tube is a thin but substantially rigid element that supports the adjacent part of the small diameter sleeve, to maintain a substantially constant flow gap relative to the needle. The sleeve can be of a soft polymeric material, while the insert is advantageously but not necessarily of an extrudable, thermally resistance material. The needle may have a curved or angled tip in some combination, and while usually used with ultrasonic energization, will often be employed in a non-ultrasonic mode but with aspiration and irrigation.

BRIEF DESCRIPTION OF THE DRAWINGS

The features and advantages of the present invention will be better understood with reference to the following description, appended claims, and accompanying drawings, wherein:

FIG. 3 is a cross-sectional view of the device of FIGS. 1 and 2;

FIG. 4 is a fragmentary perspective and some idealized view of the device of FIGS. 1–3 when partially inserted.

DETAILED DESCRIPTION

Figure 1:
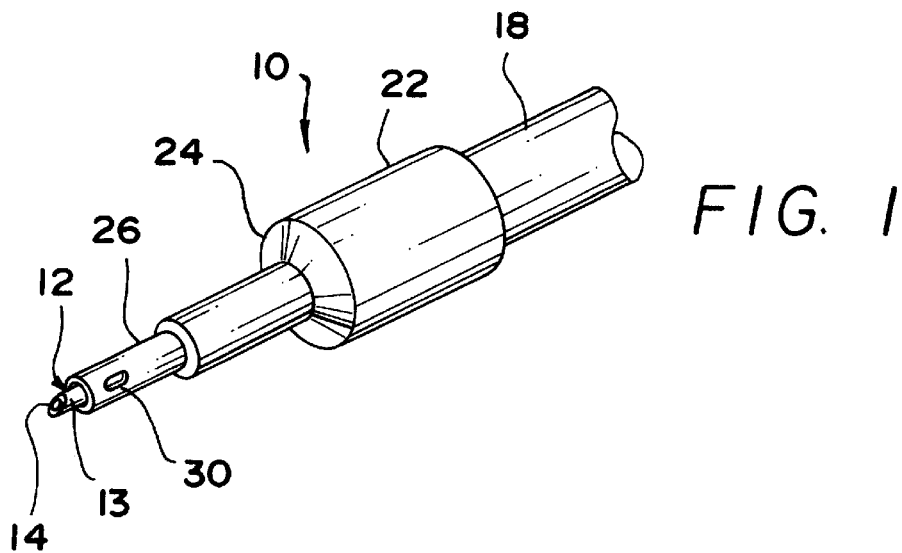
FIG. 1 is a perspective view of a device in accordance with the present invention.
Figure 2:
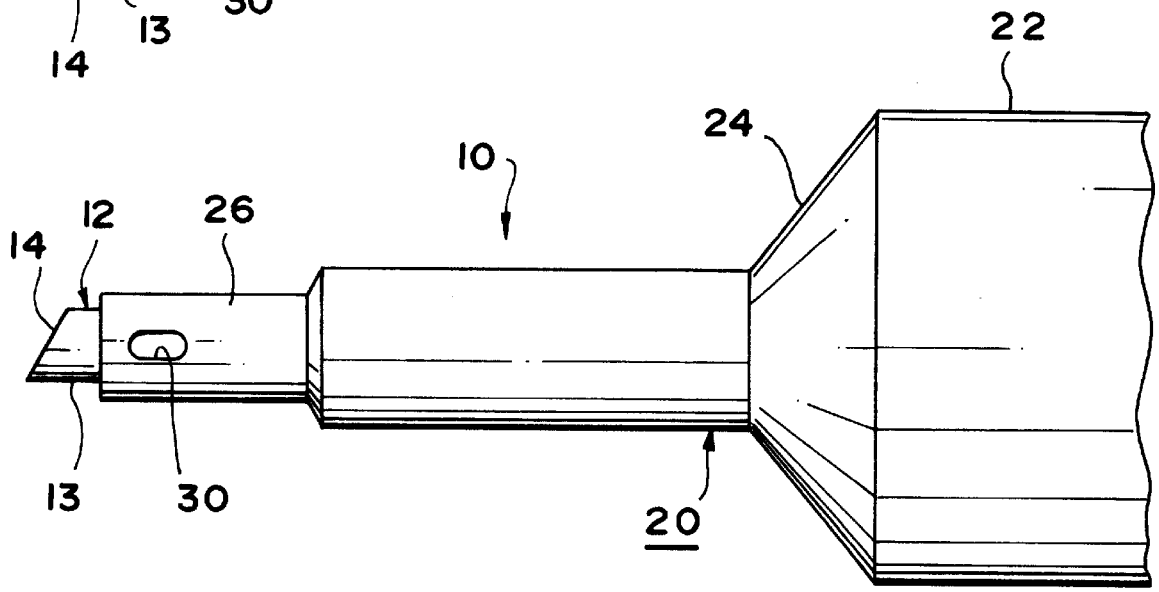
FIG. 2 is a side view of the device of FIG. 1.

An ultrasonic surgical device 10, as employed for phaco-emulsification, referring now to FIGS. 1–4, comprises a central needle having a hollow small bore tip 13 with a cutting edge 14 at the distal end. The proximal end of the needle is an enlarged hub 16 threaded into a base 18 which extends to the handpiece (not shown) and which includes a central aspiration conduit and irrigation feeder conduits (not shown) encompassing the small bore tip 13. A sleeve 20 fabricated from a flexible, polymeric material such as silicone rubber encompasses the needle 12 from the base 18 to adjacent the cutting edge 14. The sleeve 20 includes an enlarged bore portion 22, a conical transition portion 24 and small bore portion 26. The enlarged bore portion 22 of the sleeve 20 seats on the base 18 securely with moderate stretching because of its resiliency and proper diametrical size relation. In practice, such needles can have a base of a given diameter, although the diameter of the tip portion can vary (this specifies the needle size). The transition portion 24 leads to the distal small bore portion 26, which encompasses the majority of the length of the tip 13, extending close to but not covering the cutting edge 14. Adjacent the distal end, the sleeve 20 includes at least one transverse opening 30 to direct a substantial portion of the irrigation flow outwardly, so as to limit counter-current effects relative to the aspiration flow and to improve the ratio of aspiration to irrigation flow in the needle 13.

The sleeve 20 also includes a substantially rigid tubular element 32, in the nature of a stent, which is located inside the interior of, and expands, the small bore portion 26 thus forming a medium bore portion adjacent to the small bore portion of the transition portion. The stent 32 can be fabricated from a metal such as stainless steel or titanium, a hard plastic, or other suitable material in tube or spring form. However, it is preferred to employ a thermally resistant plastic such as "Kapton", a polyamide which is extrudable and has good mechanical properties. In a practical example, the thickness of the stent is preferably small, so as to minimize the size of the incision needed to receive the sleeve as well as the needle. The outer diameter is chosen to be larger than the inner diameter of the distal portion 26 of the sleeve 20. The sleeve inner diameter is approximately 0.060", as is typically the case. The stent is in the range of about 0.061" to 0.080", with a diameter of 0.065" used in a practical example. This frictionally engages the stent 32 in the sleeve 20, providing secure retention and maximizing flow. The range of thickness in practical examples is from about 0.001" to about 0.020" with 0.005" being typical. The stent 32, and therefore, the expanded part of the portion 26 about the stent 32, has a length, in relation to the total length of the small bore portion 26, of about 25% to 90%, specifically 60% to 70% in this example. With a small bore portion 26 of ½" in length, the stent is 0.3" in length. The stent 32 should not cover the transverse flow openings 30 adjacent the distal end of the sleeve 20. However, depending upon the particular surgical application, other tip sizes, lengths and ratios may be used.

This combination allows the exterior of the medium bore portion to contact and seal against the incision when the device 10 is inserted into an incision. As seen in FIG. 4, wherein the needle 12 is only partially inserted, the distal end of the sleeve 20 is free to compress axially when it engages tissue but it is not radially constrained so as to limit flow, either axially from the radial gap or from the transverse side aperture 30. Collapse of the sleeve 20 and constriction of the irrigation fluid channel is prevented.

It should be understood that the configuration shown in FIGS. 1 to 4 of the larger transition and small bore portions are merely exemplary. They may be configured in any design which is compatible with known ultrasonic surgical tool devices, such as those having curved or angled tips.

The flexible polymeric sleeve can be specially molded but this configuration has the advantage that several commercially available sleeves can be used for many applications, considerably reducing costs.

Figure 5:
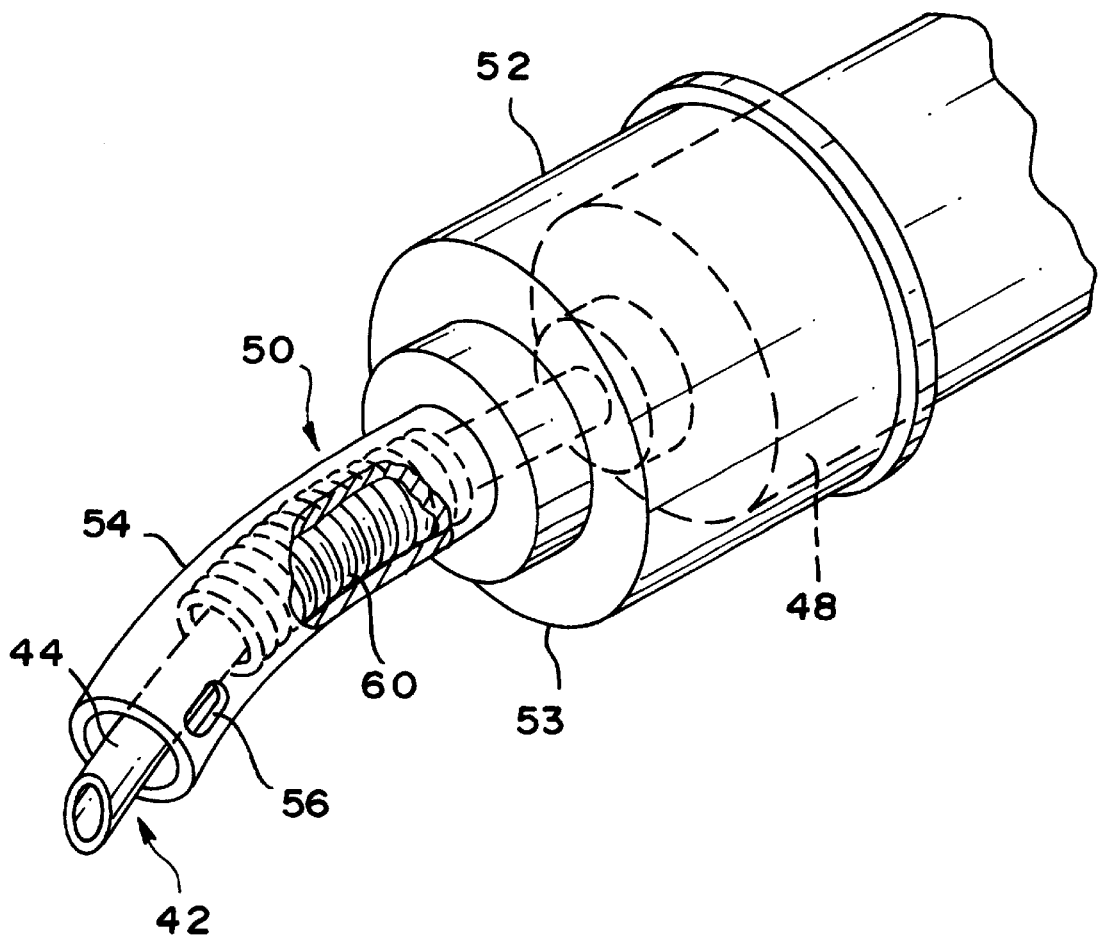
FIG. 5 is a perspective view, partially broken away, of a surgical aspiration needle with a curved tip used in conjunction with a spring supported sleeve combination in accordance with the invention.

FIG. 5 depicts a device in which a needle 42 has a curved tip or distal portion 44 extending from its base 48. Aspiration needles with curved or angled ends are useful in some applications since regions to the side of an incision can more readily be emulsified and aspirated. The shielding sleeve 50 has a large bore portion 52 engaged by interior threads (not shown) on the base 48, and a transition section 53 leading to a small diameter distal portion 54 which includes transverse flow openings 56 near the end. As in the example of FIGS. 1–4, the distal portion 54 of the sleeve 50 has a larger inner diameter than the outer diameter of the curved tip to provide a radial flow gap but the curvature of the tip introduces other considerations. The distal end of the sleeve encounters different reactive forces as the needle is inserted and used, than with a straight needle tip, and in some device attitudes and motions, the flow path may more readily be closed. Radial rigidity but a degree of axial flexibility is supplied by a frictionally engaged stent 60 of light spring material, such as stainless steel or titanium, within a proximal length of the distal portion 54. The length of stent 60 again does not reach the transverse flow opening 56. With this reinforcement, a substantial radial flow gap is maintained even though there may be contact along one side of the tip. The sleeve 50 can be fabricated with a straight or precurved distal end, but in either case will deflect to slide onto the needle 42 into operating position.

The sleeve-shielded needle of the present invention is suitable for use with any body tissue surgical tool, ultrasonic or otherwise, where maintenance of irrigation and aspiration flows through an incision is required. It prevents collapse of the sleeve and blockage of the irrigation fluid channel, and thereby maximizing irrigation flow. If ultrasonic energization of the needle is used, the maximized irrigation flow dissipates heat and limits thermal buildup. Additionally, the device maintains yielding contact with the periphery of an incision, thereby reducing leakage from the incision. It should be noted that a small amount of leakage from the incision is permissible to assist in cooling the tissue around and contacting the sleeve.

An additional advantage of the present invention is that the sleeve is capable of withstanding a large amount of pressure without collapsing. As a result a given device can often be used with a smaller than nominal incision, such as 2.5 mm, where 3 mm is usually used. Use in a smaller incision size can result in greater pressure being placed on the exterior of the sleeve as the incision stretches to accommodate the incision size, but this is withstood by the stent-reinforced section.

The above description of preferred forms of the present invention are for illustrative purposes. Variations will be apparent to those skilled in the art. In addition the invention can be practiced in the absence of any element not specifically disclosed. The scope of the invention is defined in the following claims.

What is claimed is:

1. A shielding sleeve for use with a surgical aspirating needle having a small diameter insertion end to maintain an irrigation flow about the needle in a counter current relation to a central aspiration flow entering through the distal tip of the needle as the needle is used while inserted into eye tissue through an incision, comprising:

a sleeve of flexible material adapted to be coupled to and adapted to encompass a principal portion of the length of the needle exclusive of the distal tip, the sleeve including a distal portion adapted to encompass the insertion end and the interior surface thereof having a nominal spacing from the exterior of the needle that forms a flow gap for irrigation fluid, a distal portion including at least one transverse flow aperture adjacent the distal end thereof; and an internal radially rigidifying element within the proximal length of the distal portion of the sleeve, the exterior of the rigidifying element being frictionally engaged against the interior surface of the sleeve and having an outer diameter relatively greater than the inner diameter of the distal portion of the sleeve and terminating short of the end of the distal portion while the interior surface of the rigidifying element is sized relative to the exterior of the needle to provide a predetermined flow gap therebetween despite inward pressure on the sleeve from the walls of the insertion receiving the needle and sleeve, and wherein the radially rigidifying element is 25% to 90% of the length of the distal portion and terminates short of the at least one flow aperture.

2. A sleeve as set forth in claim 1 above, wherein the rigidifying element comprises a tubular member of plastic frictionally engaged in the distal portion and having a wall thickness in the range of 0.001" to 0.020".

3. A sleeve as set forth in claim 2 above, wherein the tubular member is of "Kapton" and has a wall thickness of about 0.005", wherein the length of the tubular member is about 65% of the length of the distal portion of the sleeve, and wherein the outer diameter of the tubular member is in the range of 1–35%, greater than the unexpanded inner diameter of the distal portion of the sleeve.

4. A sleeve as set forth in claim 1 above, wherein the radially rigidifying element comprises a metal spring having axial flexibility, an external diameter greater than the unexpanded internal diameter of the distal portion of the sleeve and an inner diameter substantially corresponding to that of the inner diameter of the distal portion, to maintain the nominal spacing of the flow gap when the needle is inserted into the eye tissue.

5. A sleeve-shielded needle for use with a surgical apparatus, the needle and shielding sleeve being insertable via an incision into a site in which liquid flowing in is to be aspirated out, comprising:

a needle having a tubular tip including a central aspiration bore, and a distal cutting edge;

a cylindrical sleeve of compressible material encompassing the tubular tip through a principal portion of its length but terminating at a distal end short of the cutting edge; the sleeve being radially dimensioned relative to the exterior surface of the needle to provide a flow gap between the interior surface of the sleeve and the exterior surface of the needle for irrigation fluid flow about the needle and outwardly at the distal end of the sleeve;

a radially supportive tubular element disposed within the sleeve, the exterior surface of the tubular element being frictionally engaged against the interior surface of the sleeve over a length spaced apart from the distal end of the sleeve, the interior surface of the tubular element being sized relative to the exterior surface of the needle to maintain a spacing therebetween, in the event of inwardly directed forces applied to the sleeve, the length of the sleeve providing a flow gap between the interior surface of the sleeve and the exterior surface of the needle along the needle to adjacent the distal end of the sleeve that is substantially unaffected by inward pressure on the sleeve.

6. A sleeve-shielded needle for use with a surgical apparatus, comprising:

a needle having a tubular tip including a central aspiration bore and a distal cutting edge;

a cylindrical sleeve of compressible material encompassing the tubular tip through its length but terminating at a distal end short of the cutting edge; the sleeve being radially dimensioned to provide a flow gap between the interior surface of the sleeve and the exterior surface of the needle for irrigation fluid flow about the needle, wherein the sleeve includes at least one transverse aperture for irrigation fluid adjacent its distal end;

a radially supportive tubular element, the exterior surface of the element being frictionally engaged against the interior surface of the sleeve over a length spaced apart from the distal end of the sleeve, the length of the sleeve providing a predetermined flow gap between the interior surface of the sleeve and the exterior surface of the needle that is substantially unaffected by inward pressure on the sleeve, wherein the radially supportive tubular element has a length of from 50% to 90% of the cylindrical sleeve and an inner dimension providing a substantially constant flow gap about the tubular tip of the needle, a portion of the sleeve distal to the tubular element comprising a resilient material axially compressible against and conformable to walls of an incision.

7. A sleeve as set forth in claim 6 above, wherein the tubular element is of a high temperature plastic and has an outer diameter slightly greater than the unexpanded inner diameter of the sleeve for frictionally engaging the sleeve, and an inner diameter greater than the outer diameter of the tubular tip for maintaining the flow gap.

8. A sleeve as set forth in claim 6 above, wherein the tubular element comprises a metal spring having axial flexibility and an inner diameter dimensioned to maintain a substantial flow gap about the tubular tip of the needle.

9. A combination for maintenance of aspiration and irrigation flows in a sleeve-protected needle that is to be operated with ultrasonic vibration when the needle is held in position through a tissue incision for ophthalmic surgery, comprising:

a needle having a cylindrical tip with a central bore for aspirated fluid, and a distal cutting end;

a base coupled to the needle at the proximal end thereof;

a sleeve of soft polymeric material coupled to the base and extending in the distal direction therefrom, the sleeve including a cylindrical small bore distal end encompassing the cylindrical tip of the needle at a spacing providing a selected flow gap for irrigation fluid therebetween, the distal end terminating short of the cutting edge;

a radially supportive tubular element within the sleeve and about the needle, the tubular element having a length of from 25% to 90% of the length of the cylindrical distal end of the sleeve and spaced from the distal end, the radius of the tubular element maintaining the flow gap and the tubular element expanding the cylindrical distal end of the sleeve to increase the flow rate of irrigation fluid in the flow gap; and wherein the sleeve of soft polymeric material minimizes gaps between the sleeve and the edges of the tissue at the incision and reduces the leakage of fluid from within the incision.

10. A combination as set forth in claim 9 above, wherein the sleeve is of silicone rubber and has at least one transverse flow aperture adjacent its distal end and the tubular element has a length of about 65% of that of the small bore distal end and does not cover the transverse flow aperture.

* * * * *